(12) United States Patent
Liu

(10) Patent No.: US 8,567,271 B2
(45) Date of Patent: Oct. 29, 2013

(54) VERTICAL MOVEMENT DEVICE FOR AN EXAMINING TABLE

(75) Inventor: Jian Liu, Shanghai (CN)

(73) Assignee: Siemens Aktiengesellschaft, München (DE)

(*) Notice: Subject to any disclaimer, the term of this patent is extended or adjusted under 35 U.S.C. 154(b) by 505 days.

(21) Appl. No.: 12/856,925

(22) Filed: Aug. 16, 2010

(65) Prior Publication Data

US 2011/0041633 A1  Feb. 24, 2011

(30) Foreign Application Priority Data

Aug. 18, 2009  (CN) ..................... 2009 2 0170729 U

(51) Int. Cl.
*A61G 7/00* (2006.01)
*A47B 23/00* (2006.01)

(52) U.S. Cl.
USPC ............. 74/89.23; 5/601; 5/611; 108/144.11; 108/147.19

(58) Field of Classification Search
USPC .......................... 74/89.23, 89.34; 5/601, 611; 108/144.11, 147, 147.19
See application file for complete search history.

(56) References Cited

U.S. PATENT DOCUMENTS

| | | | | |
|---|---|---|---|---|
| 1,792,339 A | * | 2/1931 | Weidner | 254/103 |
| 3,888,464 A | * | 6/1975 | Felsen | 254/425 |
| 5,172,442 A | * | 12/1992 | Bartley et al. | 5/611 |
| 5,903,940 A | * | 5/1999 | Volker et al. | 5/611 |

FOREIGN PATENT DOCUMENTS

| | | | |
|---|---|---|---|
| CH | 662 973 | * | 11/1987 |
| WO | WO 95/31171 A1 | | 11/1995 |

OTHER PUBLICATIONS

German Office Action dated Jul. 26, 2011 for corresponding German Patent Application No. DE 10 2010 039 459.9 with English translation.

* cited by examiner

*Primary Examiner* — William C Joyce
(74) *Attorney, Agent, or Firm* — Lempia Summerfield Katz LLC

(57) ABSTRACT

A vertical movement device for an examining table includes a driving wheel, a nut and screw pair and a direction-converting synchronization belt. The driving wheel is disposed on the examining table. The rotation axis of the nut is perpendicular to the rotation axis of the driving wheel, and the nut moves vertically on the screw when the nut rotates so as to carry the examining table to move vertically. The direction-converting synchronization belt converts the rotation of the driving wheel into the rotation of the nut so as to realize the vertical movement of the examining table. The self-locking vertical movement device reduces the noise and manufacturing costs, simplifies the structure, increases the maximum lifting weight and speeds up the lifting/lowering process.

5 Claims, 2 Drawing Sheets

VERTICAL MOVEMENT DEVICE FOR AN EXAMINING TABLE

This application claims the benefit of CN 200920170729.8 filed Aug. 18, 2009, which is hereby incorporated by reference.

BACKGROUND

The present embodiments relate to a vertical movement device for an examining table.

The examining tables for high-end magnetic resonance imaging medical diagnosis systems may include vertical lifting/lowering functions, and in view of the different weights of subjects to be examined, the tables may be able to lift a relatively large working weight (e.g., >250 kg or >300 kg), so as to meet different operation requirements. The tables may also have a relatively high vertical moving speed (e.g., >35 mm/s) to reduce the examination time. Furthermore, such vertical movement structures may have self-locking functions to ensure the safety of the subjects to be examined.

A transmission mechanism set may be used to accomplish such a heavy-load, high-speed vertical movement with the self-locking function, and the transmission mechanism may have a relatively high transmission efficiency to make the examining table reach the magnet's examination height as quickly as possible. The self-locking function for stability would sacrifice the transmission efficiency, and a low transmission efficiency, in turn, would lead to an increase in noise (e.g., up to 65-70 dBA). In a medical diagnosis system, noises may make the subjects examined feel nervous and anxious, which is disadvantageous to high quality accurate diagnosis.

FIG. 1 is an isometric view of a vertical movement structure for an examining table of the prior art. As shown in the figure, a central zone for medical examination is provided in the middle of a magnet 50, and an examining table 51 can enter or exit the central zone along a horizontal direction as indicated by arrow H. The end of the examining table close to the magnet 50 may be the front end of the examining table, and the end of the examining table away from the magnet 50 may be the back end of the examining table. A driving motor 52 is may be provided near the back end of the examining table 51, a driving wheel 53 is disposed on the output shaft of the driving motor 52, and a synchronization belt 54 is wound around and between the driving wheel 53 and a driven wheel 55. The driven wheel 55 is also disposed on the examining table 51, and the rotation axis of the driven wheel 55 is parallel to the rotation axis of the driving wheel 53.

FIG. 2 shows a locally enlarged isometric view of the parts marked as number 2 in FIG. 1. In order to clearly show the transmission structure, some structures such as, for example, the synchronization belt are not shown in FIG. 2. As shown in FIG. 2, the rotation of the driven wheel 55 rotates a worm 56 that is carried coaxially with the driven wheel. The worm 56 rotates a worm wheel 57 that is engaged with the worm 56. The rotation direction of the worm wheel 57 is perpendicular to the rotation direction of the worm 56.

Referring again to FIG. 1, the worm wheel 57 is connected to a nut 58. When the worm wheel 57 rotates, the nut 58 rotates with the worm wheel 57, and at the same time, the nut 58 moves on a screw 59 (e.g., the screw 59 being fixed on a base 40). The nut 58 moves on the screw 59 along the direction indicated by arrow V in FIG. 1, so as to carry the examining table 51 and move the examining table 51 vertically.

When using this transmission mechanism set, the transmission efficiency and the self-locking function of the worm wheel 57 and the worm 56 restrict each other. Thus, improving the transmission efficiency of the worm wheel 57 and the worm 56 leads to a reduction of the self-locking performance of the worm wheel 57 and the worm 56. Currently, the overall transmission efficiency of such a transmission mechanism set is approximately 26%, and the low transmission efficiency is one of the reasons for loud noises. The maximum lifting weight of the structure shown in FIG. 1 is approximately 200 kg, and a larger lifting weight may cause a motor power overload, also increasing the noise significantly. The nut 58 and the screw 59 also need a higher transmission efficiency to meet the requirements of the moving speed of the examining table, which requires the screw 59 to have more thread heads (e.g., up to seven thread heads). The above situation makes the manufacturing of the vertical movement device for an examining table more difficult, the precision requirements stricter and the manufacturing costs higher.

SUMMARY AND DESCRIPTION

The present embodiments may obviate one or more of the drawbacks or limitations in the related art. For example, a self-locking vertical movement device for an examining table, which reduces noise and manufacturing costs, simplifies the structure, increases the maximum lifting weight and speeds up the lifting/lowering process is provided.

In one embodiment, a vertical movement device for an examining table includes a driving wheel, a nut and screw pair and a direction-converting synchronization belt. The driving wheel may be disposed on the examining table. The rotation axis of the nut is perpendicular to the rotation axis of the driving wheel, and the nut moves vertically along the screw when the nut rotates and carries the examining table to move the examining table vertically. The direction-converting synchronization belt converts the rotation of the driving wheel into the rotation of the nut so as to realize vertical movement of the examining table.

In one embodiment of the vertical movement device for an examining table, the vertical movement device includes a reduction wheel, a reduction synchronization belt and a vertical driving wheel. The diameter of the reduction wheel is larger than the diameter of the driving wheel, and the rotation axis of the reduction wheel is parallel to the rotation axis of the driving wheel. The reduction synchronization belt is wound around and between the reduction wheel and the driving wheel. The vertical driving wheel is installed coaxially with the reduction wheel, with the direction-converting synchronization belt converting the rotation of the vertical driving wheel into the rotation of the nut so as to realize vertical movement of the examining table.

In another embodiment of the vertical movement device for an examining table, the vertical movement device includes a vertical driven wheel rotating coaxially with the nut, and the direction-converting synchronization belt is wound around and between the vertical driving wheel and the vertical driven wheel.

In one embodiment of the vertical movement device for an examining table, the diameter of the vertical driving wheel is smaller than the diameter of the reduction wheel.

In another embodiment of the vertical movement device for an examining table, the direction-converting synchronization belt is a flexible rubber belt with a glass fiber core.

Since the structure of a direction-converting synchronization belt directly driving a screw is used in the vertical movement device of the present embodiments to replace the intermediate worm wheel and worm structure, the transmission efficiency is increased, the structure is simplified, noise is reduced, and the maximum lifting weight is also increased.

The self-locking function is realized by using the screw and the nut, and high-speed vertical lifting/lowering is realized by increasing the rotational speed of the nut.

In the vertical movement device of the present embodiments, the vertical moving speed of the examining table may be adjusted by changing the diameter ratios between the nut and the driving wheel, the reduction wheel and the vertical driving wheel.

Due to the increase in the transmission efficiency, the vertical movement device of the present embodiments is capable of lifting bigger weights and meeting the requirements of different subjects to be examined without changing other influencing conditions such as, for example, the driving motor.

DETAILED DESCRIPTION OF THE DRAWINGS

The present embodiments are illustrated by reference to the accompanying drawings, in which the same numerals indicate the same or similar parts. In order to clearly show the structures and mutual relationships of various parts, the proportional relationships of the parts in the accompanying drawings are only illustrative and do not represent the proportional relationship of the real structure.

Figure 1:
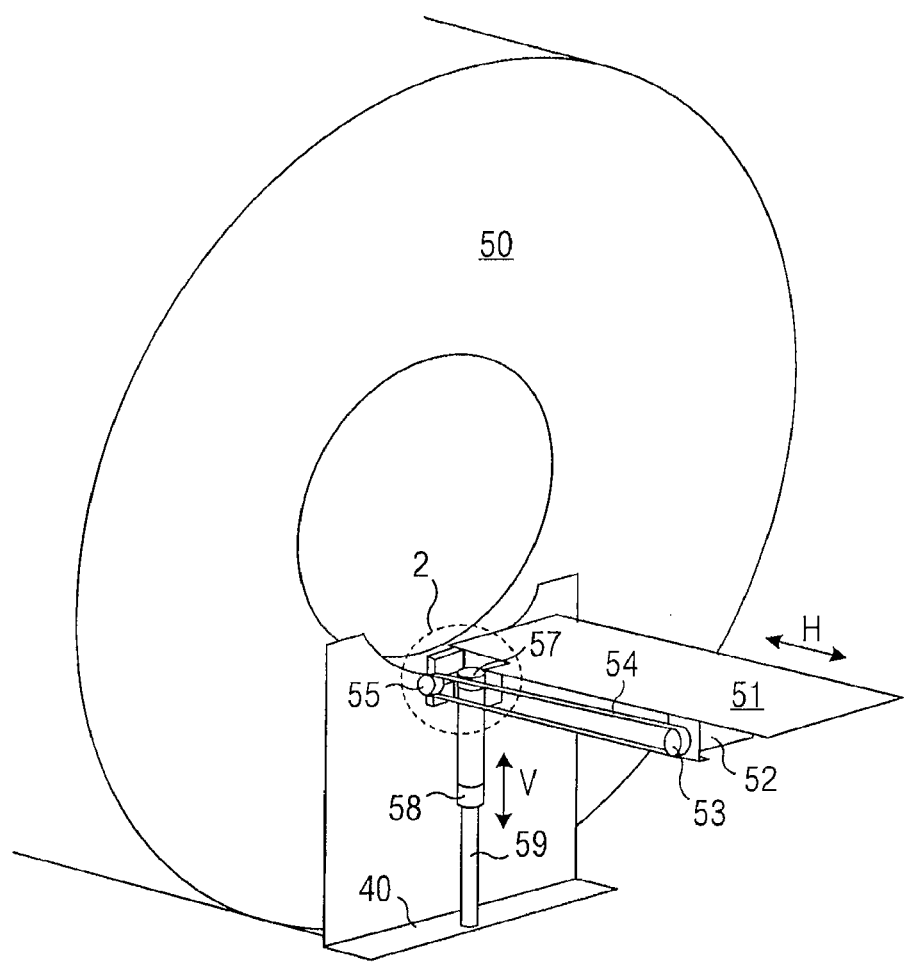
FIG. 1 is an isometric view of a prior art vertical movement device for an examining table.
Figure 2:
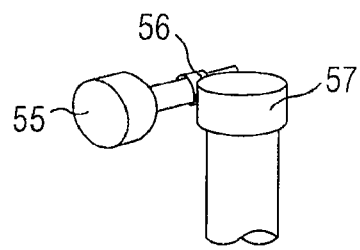
FIG. 2 is a locally enlarged isometric view of the parts identified as number 2 in FIG. 1.
Figure 3:
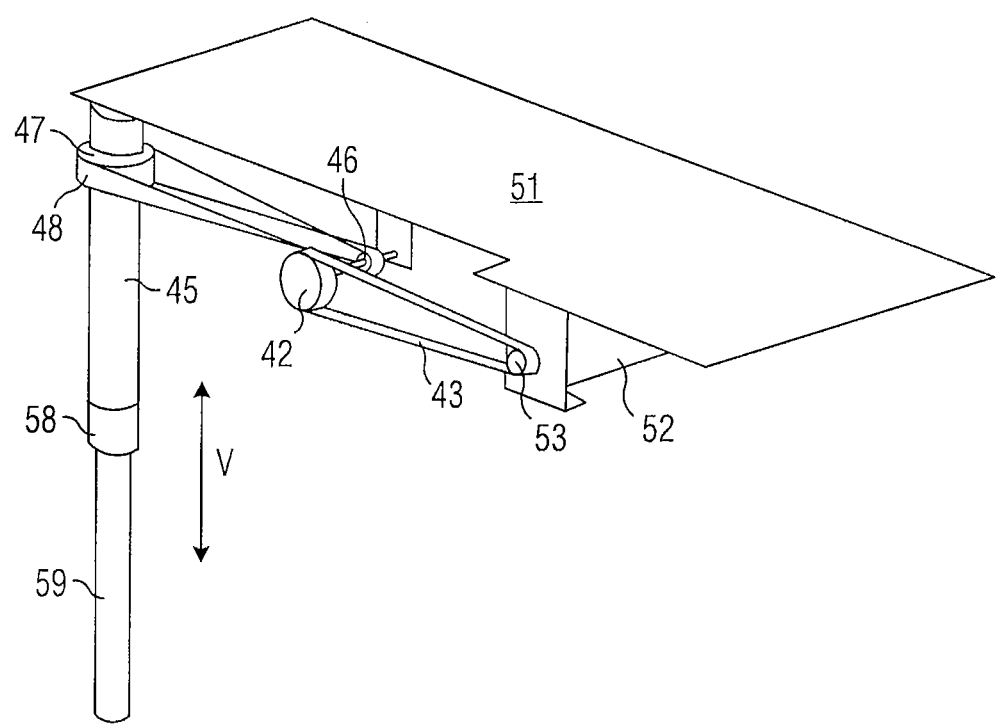
FIG. 3 is an isometric view of one embodiment of a vertical movement device for an examining table.

FIG. 3 is an isometric view of one embodiment of a vertical movement device for an examining table. The examining table 51 may be either an examining table or a part fixed on the examining table 51 and moving therewith (e.g., a bracket or a support).

As shown in FIG. 3, a driving motor 52 is disposed at a back end of the examining table 51, and a driving wheel 53 is disposed on an output shaft of the driving motor 52. A front end of the examining table 51 has a vertical driven wheel 47, and the direction of the rotation axis of the vertical driven wheel 47 is aligned to the direction of the vertical movement of the examining table 51. The driving wheel 53 may have a one level speed-reducing transmission, as shown in FIG. 3, and may be connected to the vertical driven wheel 47. Referring to FIG. 3, a reduction wheel 42 is disposed on the examining table 51, and the rotation axis of the reduction wheel 42 is parallel to the rotation axis of the driving wheel 53. The diameter of the reduction wheel 42 is larger than the diameter of the driving wheel 53, and a reduction synchronization belt 43 is wound around and between the driving wheel 53 and the reduction wheel 42. When the driving wheel 53 rotates, the driving wheel 53 carries the reduction wheel 42 in rotation via the reduction synchronization belt 43. After the one level speed-reducing transmission, the rotational speed of the reduction wheel 42 is less than the rotational speed of the driving wheel 53. The transmission speed ratio may be adjusted by changing the diameter ratio of the driving wheel 53 to the reduction wheel 42. A vertical driving wheel 46 is disposed on the rotation axis of the reduction wheel 42, and a direction-converting synchronization belt 48 is wound around and between the vertical driving wheel 46 and the vertical driven wheel 47 to convert the rotation of the vertical driving wheel 46 into the rotation of the vertical driven wheel 47. In one embodiment, the driving wheel 53 may also be directly connected to the vertical driven wheel 47 via a direction-converting synchronization belt, without a reduction transmission device.

The vertical driven wheel 47 may be a part of a nut 58 or, as shown in FIG. 3, connected to the nut 58 via a sleeve 45, so as to realize the coaxial rotation of the nut 58. When the nut 58 is rotated, the nut 58 moves simultaneously on a screw 59 along the direction indicated by arrow V in FIG. 3 to carry the examining table 51 and to move the examining table 51 vertically.

Since the rotation axis of the vertical driving wheel 46 is perpendicular to the axial direction of the vertical driven wheel 47, the direction-converting synchronization belt 48 will be wound around in a twisted way between the vertical driving wheel 46 and the vertical driven wheel 47. Under these operating conditions, the direction-converting synchronization belt 48 may be made of flexible rubber with a glass fiber core to provide good deformation and magnetic-resistant performance.

For further adjusting the transmission speed ratio, when in operation, the diameter ratios between the reduction wheel 42 and the vertical driving wheel 46, and between the driving wheel 53 and the vertical driven wheel 47 may be adjusted, respectively, such that the driving motor 52 may provide a continuous, stable and controllable power for the lifting/lowering of the examining table 51.

In a magnetic resonance imaging medical diagnosis system, when the examining table 51 is to be vertically lifted/lowered, the driving motor 52 rotation carries the driving wheel 53 coaxially therewith in rotation. The driving wheel 53 carries the reduction wheel 42 in rotation in the same direction via the reduction synchronization belt 43. The reduction wheel 42 carries the vertical driving wheel 46 installed coaxially therewith in rotation in the same direction. The direction-converting synchronization belt 48 carries the vertical driven wheel 47 in rotation. The vertical driven wheel 47 is connected to the nut 58, and the nut 58 rotates with the vertical driven wheel 47. The nut 58 moves on the screw 59 along the vertical direction V to carry the examining table 51, thus moving the examination table 51 vertically, so as to realize the vertical lifting/lowering of the examining table at a relatively high speed.

The vertical movement device for an examining table of the present embodiments utilizes the synchronization belt direction-converting transmission to replace the low-efficiency worm wheel and worm transmission, which significantly improves the transmission efficiency of the vertical movement device and makes the lifting/lowering speed of the examining table faster. Due to the improvement in the transmission efficiency, a larger maximum lifting weight may be realized so as to meet the operating requirements of various subjects to be examined without replacing the driving motor.

As described above, in a vertical movement device for an examining table of the present embodiments, the vertical lifting/lowering of the examining table is realized by the cooperation of direction-converting transmission between the screw and the synchronization belt. In the vertical movement structure of the present embodiments employing a one-level speed-reducing transmission, both 90 degree direction-converting of the synchronization belt is realized and high-efficiency transmission of the synchronization belt is provided (e.g., an efficiency up to 40%). Also, the structure is simple, the noise is low, and given that the moving speed of the examining table is provided, the high-efficiency and low-noise design of the vertical examining table structure with a high magnetic field ($\geq 1.5$ T) for magnetic resonance imaging medical diagnosis systems is realized. The high-speed, highload vertical movement is realized under the precondition of stable self-locking function, and a relatively high location precision of the vertical movement is provided. The above features may effectively increase the comfort level during the diagnosis and the diagnosis speed and quality of the magnetic resonance imaging medical system.

In the vertical movement device of the present embodiments, since the worm wheel and worm structure are not used, a two thread head screw may meet the requirements of the transmission efficiency, which reduces the manufacturing costs and complexity of the process and makes it easier to meet the requirements of location precision. The nut and the screw have the self-locking function, and during the magnetic resonance imaging medical examination, the structure is locked when the examining table is lifted to a certain position, thus fixing the examining table at the position for the safety of the subjects to be examined.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A vertical movement device for an examining table, the vertical movement device comprising:
    a first driving wheel disposed on the examining table;
    a nut and screw pair, wherein a rotation axis of the nut is perpendicular to a rotation axis of the first driving wheel, and the nut is operable to move vertically along the screw when the nut rotates and carry the examining table to move the examining table vertically;
    a direction-converting synchronization belt operable to convert a rotation of the first driving wheel into the rotation of the nut;
    a reduction wheel disposed on the examining table, the diameter of the reduction wheel being larger than the diameter of the first driving wheel, and a rotation axis of the reduction wheel being parallel to the rotation axis of the first driving wheel;
    a reduction synchronization belt wound around the reduction wheel and the first driving wheel; and
    a second driving wheel installed coaxially with the reduction wheel, the direction-converting synchronization belt operable to convert a rotation of the second driving wheel into the rotation of the nut.

2. The vertical movement device as claimed in claim 1, further comprising a vertical driven wheel operable to rotate coaxially with the nut, the direction-converting synchronization belt being wound around the second driving wheel and the vertical driven wheel.

3. The vertical movement device as claimed in claim 2, wherein the diameter of the second driving wheel is smaller than the diameter of the reduction wheel.

4. The vertical movement device as claimed in claim 1, wherein the diameter of the second driving wheel is smaller than the diameter of the reduction wheel.

5. The vertical movement device as claimed in claim 3, wherein the direction-converting synchronization belt comprises a flexible rubber belt with a glass fiber core.

* * * * *